US010836665B2

(12) United States Patent
Reyes et al.

(10) Patent No.: US 10,836,665 B2
(45) Date of Patent: Nov. 17, 2020

(54) SCALE INHIBITOR METHODS AND COMPOSITIONS

(71) Applicants: Dow Global Technologies LLC, Midland, MI (US); The Board of Trustees of the University of Illinois, Urbana, IL (US); Rohm and Haas Company, Philadelphia, PA (US)

(72) Inventors: Larisa Mae Q. Reyes, Lake Jackson, TX (US); J. Keith Harris, Midland, MI (US); Joshua S. Katz, Merlon Station, PA (US); Christopher J. Tucker, Midland, MI (US); Steven C. Zimmerman, Urbana, IL (US); Brittany A. Walker, Urbana, IL (US)

(73) Assignees: Dow Global Technologies LLC, Midland, MI (US); Rohm and Haas Company, Collegeville, PA (US); The Board of Trustees of the University of Illinoi, Urbana, IL (US)

( * ) Notice: Subject to any disclaimer, the term of this patent is extended or adjusted under 35 U.S.C. 154(b) by 171 days.

(21) Appl. No.: 15/757,546

(22) PCT Filed: Sep. 2, 2016

(86) PCT No.: PCT/US2016/050083
§ 371 (c)(1),
(2) Date: Mar. 5, 2018

(87) PCT Pub. No.: WO2017/044383
PCT Pub. Date: Mar. 16, 2017

(65) Prior Publication Data
US 2018/0244552 A1 Aug. 30, 2018

Related U.S. Application Data

(60) Provisional application No. 62/216,776, filed on Sep. 10, 2015.

(51) Int. Cl.
| | | |
|---|---|---|
| C02F 5/10 | (2006.01) | |
| C07C 57/34 | (2006.01) | |
| C02F 103/02 | (2006.01) | |
| C02F 103/10 | (2006.01) | |

(Continued)

(52) U.S. Cl.
CPC ............ C02F 5/10 (2013.01); C07C 57/34 (2013.01); *C02F 2103/023* (2013.01);
(Continued)

(58) Field of Classification Search
CPC .......... C02F 2103/023; C02F 2103/10; C02F 2103/16; C02F 2103/18; C02F 2103/22;
(Continued)

(56) References Cited

U.S. PATENT DOCUMENTS 6,242,499 B1    6/2001  Gruning et al.
8,821,630 B2    9/2014  Kuo et al.
(Continued)

OTHER PUBLICATIONS

Lei Ling, Yuming Zhou, Jingyi Huang, Qingzhao Yao, Guangqing Liu, Peixin Zhang, Wei Sun, Wendao Wu; Carboxylate-terminated double-hydrophilic block copolymer as an effective and environmental inhibitor in cooling water systems; Desalination 304 (2012) 33-40. (Year: 2012).*

(Continued)

*Primary Examiner* — Pranav N Patel

(57) ABSTRACT

A method of scale inhibition treatment of a water system comprising introducing an aqueous scale inhibiting composition into the water system wherein the aqueous scale inhibiting composition comprises a carboxylated hyperbranched polyglycerol.

6 Claims, 4 Drawing Sheets

(51) Int. Cl.
  *C02F 103/16* (2006.01)
  *C02F 103/32* (2006.01)
  *C02F 103/36* (2006.01)
  *C02F 103/26* (2006.01)
  *C02F 103/22* (2006.01)
  *C02F 103/18* (2006.01)
  *C02F 103/28* (2006.01)
(52) U.S. Cl.
  CPC ...... *C02F 2103/10* (2013.01); *C02F 2103/16* (2013.01); *C02F 2103/18* (2013.01); *C02F 2103/22* (2013.01); *C02F 2103/26* (2013.01); *C02F 2103/28* (2013.01); *C02F 2103/32* (2013.01); *C02F 2103/365* (2013.01)
(58) Field of Classification Search
  CPC .............. C02F 2103/26; C02F 2103/28; C02F 2103/32; C02F 2103/365; C02F 5/10; C07C 57/34
  See application file for complete search history.

(56) References Cited

U.S. PATENT DOCUMENTS

| | | |
|---|---|---|
| 8,901,246 B2 | 12/2014 | McManus et al. |
| 2009/0130006 A1 | 5/2009 | Wang et al. |
| 2010/0270022 A1* | 10/2010 | Crews ............... C09K 8/685 |
| | | 166/308.3 |
| 2011/0092743 A1 | 4/2011 | Li et al. |
| 2014/0027669 A1 | 1/2014 | Detering et al. |
| 2015/0203742 A1* | 7/2015 | Reddy ............... C09K 8/588 |
| | | 507/225 |

OTHER PUBLICATIONS

International Search Report issued in International Appln.No. PCT/US2016/050083 dated Oct. 10, 2016.

Written Opinion issued in International Appln. No. PCT/US2016/050083 dated Oct. 10, 2016.

* cited by examiner

Solutions of PAA-Na+ in 25 mL Calcium Brine

Solutions of cHPG 5 in 25 mL Calcium Brine

SCALE INHIBITOR METHODS AND COMPOSITIONS

This application is the U.S. National Stage of International Application No. PCT/US2016/050083, filed on Sep. 2, 2016, which claims the benefit of U.S. Provisional Application Ser. No. 62/216,776, filed on Sep. 10, 2015, the entire contents of both are hereby incorporated by reference.

FIELD OF THE INVENTION

The invention relates generally to a method of preventing scale in water systems using polyglycerol compositions. More specifically, the disclosed carboxy hyperbranched polyglycerol compositions of the invention are particularly suitable for applications in the presence of precipitous metal ions.

BACKGROUND OF THE INVENTION

Scale inhibiting polymers are often used in water treatment and oil field applications to minimize and/or prevent scale deposition. The deposition of scale can occur in the transport of aqueous mixtures and in subterranean rock formations due to the presence of water bearing alkaline earth metal cations such as calcium, barium, strontium and the like as well as the presence of anions such as phosphate, sulfates, carbonates, silicates and the like. When these ions are in sufficient concentrations, a precipitate can form that builds up on interior surfaces of the conduits used for transport or in the subterranean rock formations, which restrict flow of the media of interest, e.g., water or oil.

In oil field applications, scales that are commonly formed include calcium sulfate, barium sulfate, and/or calcium carbonate scales. These scales are generally formed in the fresh waters or brines used in well stimulation as a result of increased concentrations of these particular ions, the water pH, pressures, and temperatures. In addition, calcium phosphate can form in the presence of phosphates commonly used to treat wells and pipes for corrosion. The buildup of these mineral precipitates can reduce or block flow in the conduits and rock formations as well as cause other problems. In many cases, the first warning of the existence of a significant scale deposit may be a decline in well performance. In these instances, scale removal techniques may become necessary. Scaling may result in substantial repair costs and downtime in certain operations.

Scale inhibiting materials are commonly applied to rock formations by means of a squeeze treatment prior to production. In these applications, a relatively concentrated form of the scale inhibitor is added. Using the method, the scale inhibitor is pumped into a water-producing zone and attaches to the formation by chemical adsorption or by temperature-activated precipitation. When the well is put back into production, the scale inhibitor leaches out of the formation rock to provide scale inhibition.

Capillary injection is another method for delivering scale inhibiting materials. In capillary injection, a relatively concentrated form of the scale inhibitor composition is continuously pumped into the well during production.

Typical oilfield formation and produced waters are rich in divalent cations such as calcium and magnesium. Anionic scale inhibitors interact with these cations to prevent carbonate and sulfate scale formation but in the case of high calcium brines, this interaction may lead to the precipitation of stable calcium/scale inhibitor salts. These salts, often called "pseudo-scales", can cause plugging near the injection point when continuous injection treatment is applied. Additionally, if the salts do not dissolve completely upon dilution into the process stream, suspended particles may deposit in low flow areas and can act as "seeds" for carbonate and sulfate scales, increasing rather than reducing the natural scaling tendency of the produced water.

There is an ongoing need for scale inhibitor compositions useful in water systems.

BRIEF SUMMARY OF THE INVENTION

In accordance with one aspect of the invention there is provided a method of scale inhibition treatment of a water system comprising introducing an aqueous scale inhibiting composition into the water system wherein the aqueous scale inhibiting composition comprises a carboxylated hyperbranched polyglycerol. The method of the invention is also useful in aqueous systems with high ppm concentrations of total dissolved solids from the produced water.

The invention describes the use of carboxylated hyperbranched polyglycerols as scale inhibitors for treatment of an oil and gas production well and/or subterranean formation and topside equipment. The scale inhibition composition may be introduced by capillary injection and/or squeeze treatment. The carboxylate hyperbranched polyglycerol are effective as scale inhibitors even at high concentration of divalent ions. Moreover, the molecule is also believed to be biodegradable.

DETAILED DESCRIPTION OF THE INVENTION

Figure 1:
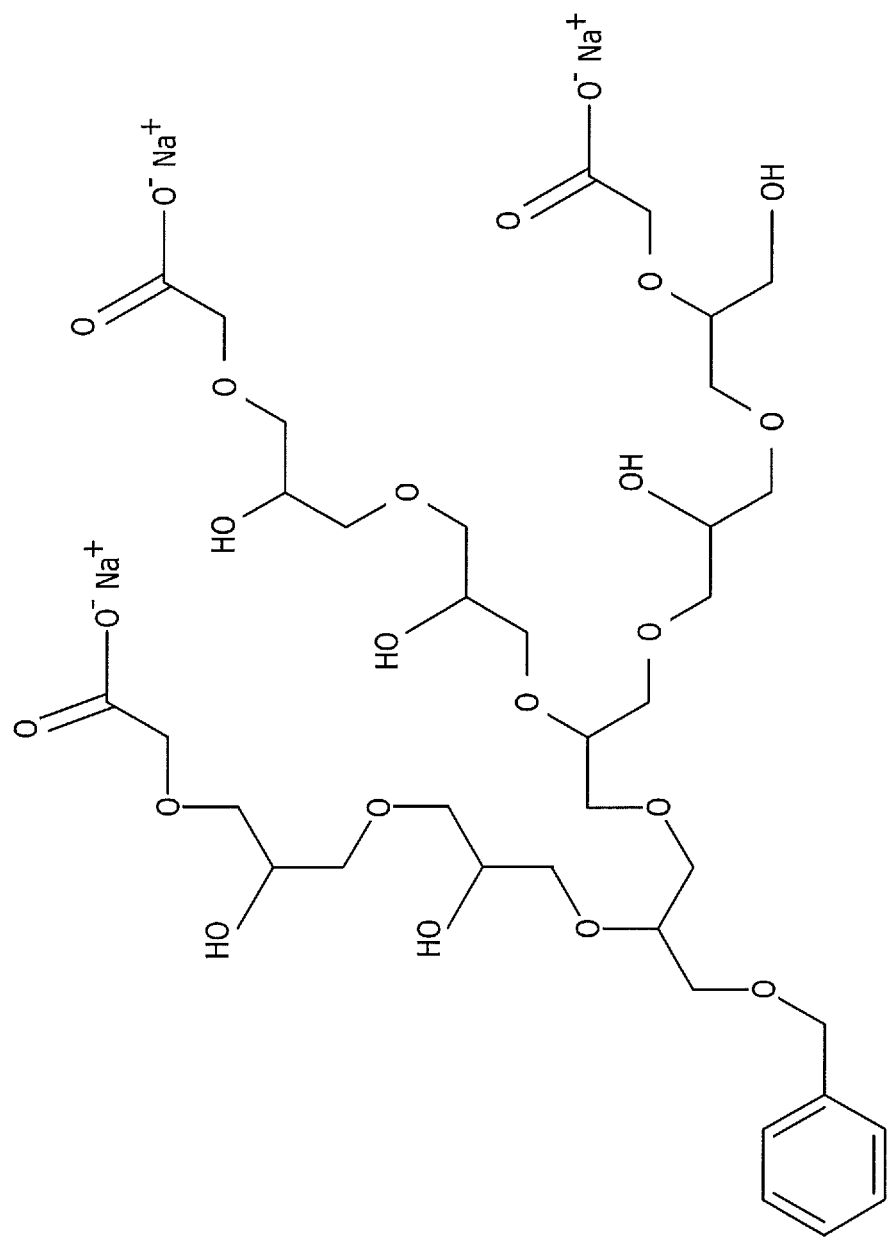
FIG. 1 is one exemplary illustration of one polymer useful in the method of the invention.

The invention is a method of treating scale to inhibit the formation thereof in a variety of water systems. The method comprises the introduction of a carboxylated hyperbranched polyglyerol into the water system in a concentration effective to inhibit scale formation.

The Polymer

Generally, carboxylated hyperbranched polyglycerols are known to those of skill in the art. Representative polyglycerols include those synthesized through any number of pathways.

One means of synthesizing polyglycerols useful in the invention includes using glycidol and a ring opening polymerization through an anionic initiator. Useful initiators may include metal amides, alkoxides, hydroxides, cyanides, phosphines, amines, etc.

One method of forming multiarm polymers includes that taught in U.S. Pat. No. 8,901,246 which is incorporated herein by reference.

Another means of synthesizing the polyglycerol compounds useful in the method of the invention is condensation of glycerol in the presence of acid catalysts at temperatures of about 175° C. or more. Time and conditions are those typical of glycerol condensation. Generally, the process includes using mono-glycerols having hydroxide functionality, forming ether linkages between the non-glycerols to obtain poly-glycerols, and carboxylating the polyglycerol polymers.

The term "carboxylation" as used herein refers to incorporation of carboxylic groups onto polyglycerol through, for example, any number of synthetic pathways. One means of carboxylating the hyperbranched polyglycerols is through alkylation or a Michael reaction. Carboxylating the hyperbranched polyglycerols by alkylation with alpha chloro acetate is also a useful means of synthesis.

Another means of carboxylating the hyperbranched polyglycerols useful in the invention includes reaction of hydroxyl (—OH) groups with carboxyl groups which can be in the form of free acid, acid anhydride, carboxylate ester, or mixtures thereof. It is known to add partial esters to polyglycerols through carboxylation, such as disclosed for example in U.S. Pat. No. 6,242,499 of Gruning et al., which is incorporated herein by reference.

Carboxylation of polyglycerols may be completed using carboxylic acids, such as a monocarboxylic acid, dicarboxylic acid or tricarboxylic acid, for example, wherein one or more carboxylic acid groups is incorporated onto polyglycerol molecules through carboxylation.

Polycarboxylic compounds contemplated for use in the invention may contain one or more carboxylic groups and can be in the form of free acid, acid anhydride, carboxylic acid ester, or carboxylate ester. For example, the carboxylic anhydride can be chosen from a group including succinic anhydride, glutaric anhydride, maleic anhydride, itaconic anhydride, crotonic anhydride, phthalic anhydride, trimellitic anhydride, or mixtures thereof. The polycarboxylic acid can be chosen, for example, from a group including oxalic acid, malonic acid, succinic acid, glutaric acid, adipic acid, pimelic acid, suberic acid, azplaic acid, sebacic acid, maleic acid, fumaric acid, glutaconic acid, muconic acid, itaconic anhydride, crotonic anhydride, phthalic acid, isophthalic acid, terephthalic acid, citric acid, isocitric acid, aconitic acid, carballytic acid, trimesic acid, trimellitic acid, nitrilotriacetic acid, ethylenediamine tetra-acetic acid, and mixtures thereof. The polycarboxylate ester can be, for example, monoester, diester or triester of the above polycarboxylic acids, and the ester can comprise an alkyl group containing one to three carbons.

Thus, a composition of the invention for inhibiting scale comprises an aqueous solution of a carboxylated hyperbranched polyglycerol polymer such as those shown in U.S. Pat. No. 8,901,246, which is incorporated herein by reference. One exemplary carboxylated polyglycerol, seen in FIG. 1, is useful in the method of the invention.

Representative conditions for carboxylation are disclosed in U.S. Pat. No. 8,821,630 issued on Sep. 2, 2014, which is also incorporated herein by reference.

The resulting polymer used in the method of the invention generally has a molecular weight ranging from about 1000 to 50,000 Da, and preferably from about 1,000 to 15,000 Da.

Preferably once in solution, the method of the invention may be conducted at pH's ranging from about 2 to 14, and more preferably 4 to 8. Temperatures of application range from 20° C. to 300° C., preferably 20° C. to 120° C., with pressures ranging from 3,000 to 35,000 psi.

The Method of the Invention

Experiments can be conducted in a laboratory to determine an effective minimum inhibitor concentration (MIC) which just inhibits inorganic scale formation under simulated production conditions. The ability of the operator to quickly and accurately determine the amount of scale inhibitor in the produced fluids and compare this to the MIC values generated allows the operator to decide when it is necessary or desirable to retreat the reservoir or increase the topside addition rate to ensure that no damage occurs to his reservoir or equipment due to inorganic scale deposition.

The effective MIC for a non-thermally aged scale inhibitor of the present invention is equal to or less than 200 ppm, more preferably equal to or less than 100 ppm, and most preferably equal to or less than 20 ppm.

According to some embodiments of the invention, the scale inhibiting polymer compositions of the invention may be used to treat scale in any water system in which scale may be likely to form. Exemplary water systems, include, without limitation, cooling tower water systems (including open recirculating, closed and once-through systems); petroleum wells, downhole formations, geothermal wells and other oil field applications; boilers and boiler water systems; mineral process waters including mineral washing, flotation and benefaction; paper mill digesters, washers, bleach plants and white water systems; black liquor evaporators in the pulp industry; gas scrubbers and air washers; continuous casting processes in the metallurgical industry; air conditioning and refrigeration systems; industrial and petroleum process water; indirect contact cooling and heating water, such as pasteurization water; water reclamation and purification systems; membrane filtration water systems; food processing streams (meat, vegetable, sugar beets, sugar cane, grain, poultry, fruit and soybean); and waste treatment systems as well as in clarifiers, liquid-solid applications, municipal sewage treatment and industrial or municipal water systems.

A preferred embodiment of the invention is a method for scale inhibition treatment of an oil or gas production well and/or subterranean formation. The scale inhibition composition of the present invention may be introduced by capillary injection and/or by a squeeze treatment.

The method of the invention is useful for solutions having high salinity and high dissolved solids. Total dissolved solids may have from at least about 2000 ppm, preferably about 4000 ppm, and more preferably, at least about 6000 ppm. The method of the invention is useful in systems having total dissolved solids as high as about 200,000 ppm, preferably as high as about 300,000 ppm, and more preferably as high as about 400,000 ppm.

Capillary injection of scale inhibitor can be carried out topside or downhole via chemical injection lines. Capillary injection at the wellhead or downhole may be needed in injector wells, especially for produced water reinjection, or in producing well streams. Capillary injection in the injector wells has also been carried out to prevent scaling in producing wells. Capillary injection into produced waters is usually carried out topside at the wellhead, where other production chemicals, such as corrosion inhibitors, may be injected. In fact, many scale inhibitors are not compatible with certain corrosion inhibitors. Scale inhibitors can also be injected downhole if a capillary string is available or via the gas lift injection system. In gas lift injection, it is important to add a low-vapor-pressure solvent (vapor pressure depressant, VPD) such as a glycol to the aqueous scale inhibitor solution to avoid excessive solvent evaporation and "gunking" of the scale inhibitor. In addition, glycol or some other hydrate inhibitor may be needed to suppress gas hydrate formation. A scale dissolver blended with a scale inhibitor has also been deployed in a gas lift system.

For capillary injection applications, the concentration of the polymer in the aqueous scale inhibitor composition of the invention is equal to or greater than 1 weight percent, preferably equal to or greater than 5 weight percent, and more preferably equal to or greater than 10 weight percent. For capillary injection applications, the concentration of the polymer in the aqueous scale inhibitor composition of the present invention is equal to or less than 60 weight percent, preferably equal to or less than 50 weight percent, and more preferably equal to or less than 20 weight percent.

The basic idea in a scale inhibition squeeze treatment is to protect the well downhole from scale deposition and formation damage. The inhibitor will, of course, continue to work above the wellhead, protecting the pipeline from scaling, but a further dose of a scale inhibitor may be needed topside. In a squeeze treatment, a solution of the scale inhibitor is injected into the well above the formation pressure whereby the inhibitor solution will be pushed into the near-well formation rock pores. The well is then usually shut in for a period of hours to allow the inhibitor to be retained, by various mechanisms, in the rock matrix. When the well is put back on stream again, produced water will pass the pores where the chemical has been retained, dissolving some of it. In this way, the produced water should contain enough scale inhibitor to prevent scale deposition. When the concentration of the inhibitor falls below the MIC (minimum inhibitor concentration that prevents scale deposition), the well should be resqueezed. Naturally, long squeeze lifetimes will keep the overall downhole scale treatment costs to a minimum.

In one embodiment, the scale inhibiting polymer composition used in a squeeze application may be diluted in a carrier solvent (usually brine) and propagated out to an optimized radial distance into the oil producing formation, where it is retained and then released slowly back into the aqueous phase during normal well production. In one embodiment, the squeeze process generally includes applying a dilute solution of the scale inhibiting polymer with surfactant (0.1 weight percent) to clean and cool the near wellbore. Once cleaned, a high concentration solution of the scale inhibiting polymer at between 5 and 20 weight percent is introduced, followed by a low concentration solution of the scale inhibiting polymer. The solutions are left in contact with the reservoir for a period of time effective to allow for adsorption equilibration, after which the well is returned to production. Adhesion to the formation allows the scale inhibiting polymer to remain within the near-wellbore area without being pumped up in the oil/water emulsion.

Although squeeze application of the chemical is one of the most common method of treating downhole scale, the product could also be applied by other techniques commonly used offshore, which include gas-lift injection, downhole annulus injection, encapsulation or soluble matrix techniques, sub-sea wellhead injection via umbilical or indeed secondary topside treatments to enhance inhibitor performance as process conditions vary scaling tendency.

In a preferred embodiment, the scale inhibiting composition of the invention is used in treating scale under high temperature and/or high pressure conditions, for example in oil or gas productions wells. The scale inhibiting compositions may be used to treat scale in conditions wherein the temperature is at least about 20° C. or in the range of about 120° C. to about 230° C. The scale inhibiting compositions also may be used to treat scale in conditions wherein the pressure is at least about 5,000 psi or in the range of about 5,000 psi to about 35,000 psi. In a particular embodiment, the scale inhibition treatment is at a temperature of about 120° C. to about 230° C. and a pressure of about 3,000 to 35,000 psi.

The scale inhibitor polymer and/or composition may be used in an amount effective to produce any necessary or desired effect. In one embodiment, an effective amount of the scale inhibitor composition of the embodiments may be dependent on one or more conditions present in the particular system to be treated and scale inhibiting moieties in the scale inhibiting polymer, as would be understood to one of skill in the art. The effective amount may be influenced, for example, by factors such as the area subject to deposition, temperature, water quantity, and the respective concentration in the water of the potential scale and deposit forming species.

For squeeze applications, the concentration of polymer in the aqueous scale inhibitor composition of the invention is equal to or greater than 5 weight percent, preferably equal to or greater than 10 weight percent, more preferably equal to or greater than 20 weight percent, more preferably equal to or greater than 30 weight percent, and more preferably equal to or greater than 40 weight percent based on the total weight of the aqueous scale inhibitor composition.

According to various embodiments, the treatment composition according to the present disclosure will be effective when the scale inhibitor polymer is used at levels equal to or less than 200 parts per million (ppm). In some embodiments, the composition is effective at concentrations of at least 1 ppm, preferably from 1 ppm to 200 ppm; and in still other embodiments; the effective concentration is 1 to about 100 ppm. In certain embodiments, the effective concentration of the polymer is equal to or less than 10 ppm, preferably equal to or less than 20 ppm, more preferably equal to or less than 30 ppm, more preferably equal to or less than 40 ppm or even more preferably equal to or less than 50 ppm. In various embodiments, the treatment composition can be added directly into the desired aqueous system to be treated in a fixed quantity provided the pH is subsequently adjusted to neutralize the polymer as noted above or can be provided as an aqueous solution and added continuously or intermittently to the aqueous system as can be desired for some applications.

EXAMPLES

The invention will now be illustrated through the following non-limiting examples.

Scale Inhibition Static Bottle Test

The scale inhibitors—carboxylated hyperbranched (cHPGs) and polyacrylic acid (PAAs) were evaluated in a test brine solution for inhibition effectiveness. The evaluations are done at 5 varying concentrations: 1, 10, 20, 100 and 200 ppm of the scale inhibitor (based on % actives).

Preparation of Test Brine Solution.

The composition of the test brine solution for evaluating scale inhibition effectiveness for the cHPGs and PAA is made up in accordance with NACE TM0374 method and is a combination of a calcium-containing brine solution and a sulfate-containing brine solution. A 1,000 mL calcium-containing brine solution is prepared by adding 11.10 g $CaCl_2 \cdot 2H_2O$, 7.50 g NaCl and dissolving to 1,000 mL with deionized water. A 1,000 mL sulfate-containing brine is prepared by adding 10.66 g $Na_2SO_4$ and 7.50 g NaCl and dissolving to 1,000 mL with deionized water. For both cHPGs and PAA, a 1000 ppm aqueous stock solution of the scale inhibitor is made in a 250 mL plastic bottle using deionized water.

Scale Inhibitor Sample Preparation for Scale Inhibition Evaluation.

Into a 125 mL glass bottle is added 50 mL of each calcium-containing; brine and the sulfate-containing brine stock solutions. To the 100 mL test brine solution is added the appropriate amount from the cHPGs and PPA 1,000 ppm stock solutions to provide the cHPGs and PAA brine solutions comprising scale inhibitor at 1, 10, 20, 100, and 200 ppm. After addition of the scale inhibitor the bottles are capped and immediately agitated to mix the contents. Duplicate test solutions are prepared for each sample. A blank solution of brine (50 mL of each brine solution) with no scale inhibitor is also prepared, capped, and agitated. The test bottles are placed in an oil bath at about 70° C. for 24 hours. Then removed and cooled to ambient temperature for a time not to exceed two hours.

Inductively Coupled Plasma (ICP) Testing.

Scale inhibition is determined by ICP. The following procedure is followed to prepare the samples for ICP analysis:
1. Add approximately 1 g of inhibitor solution via a filtered syringe into a 50 mL ICP vial.
2. Dilute the sample to approximately 40 g with a solution of 0.25 N HCl,
3. Add approximately 0.5 g of the calcium-containing brine stock solution to 40 g with 0.25 N HCl for use as blank reference samples,
4. Cap each ICP vial and mix the contents well,
5. Record the weights of each sample, and
6. Determine calcium ion concentration.

The calcium ion concentrate for each sample is determined by ICP. According to the NACE TM0374 method calcium ion concentration values for duplicate samples often differ by 2 percent or more. A 5% difference in calcium ion concentration is considered unacceptable and this result is discarded and the test repeated.

Percent Inhibition is calculated according to the following formula:

$$\frac{[Ca] \text{ final treated concentration} - [Ca] \text{ blank after precip}}{[Ca] \text{ blank before recip} - [Ca] \text{ blank after precip}} \times 100$$

Figure 2:
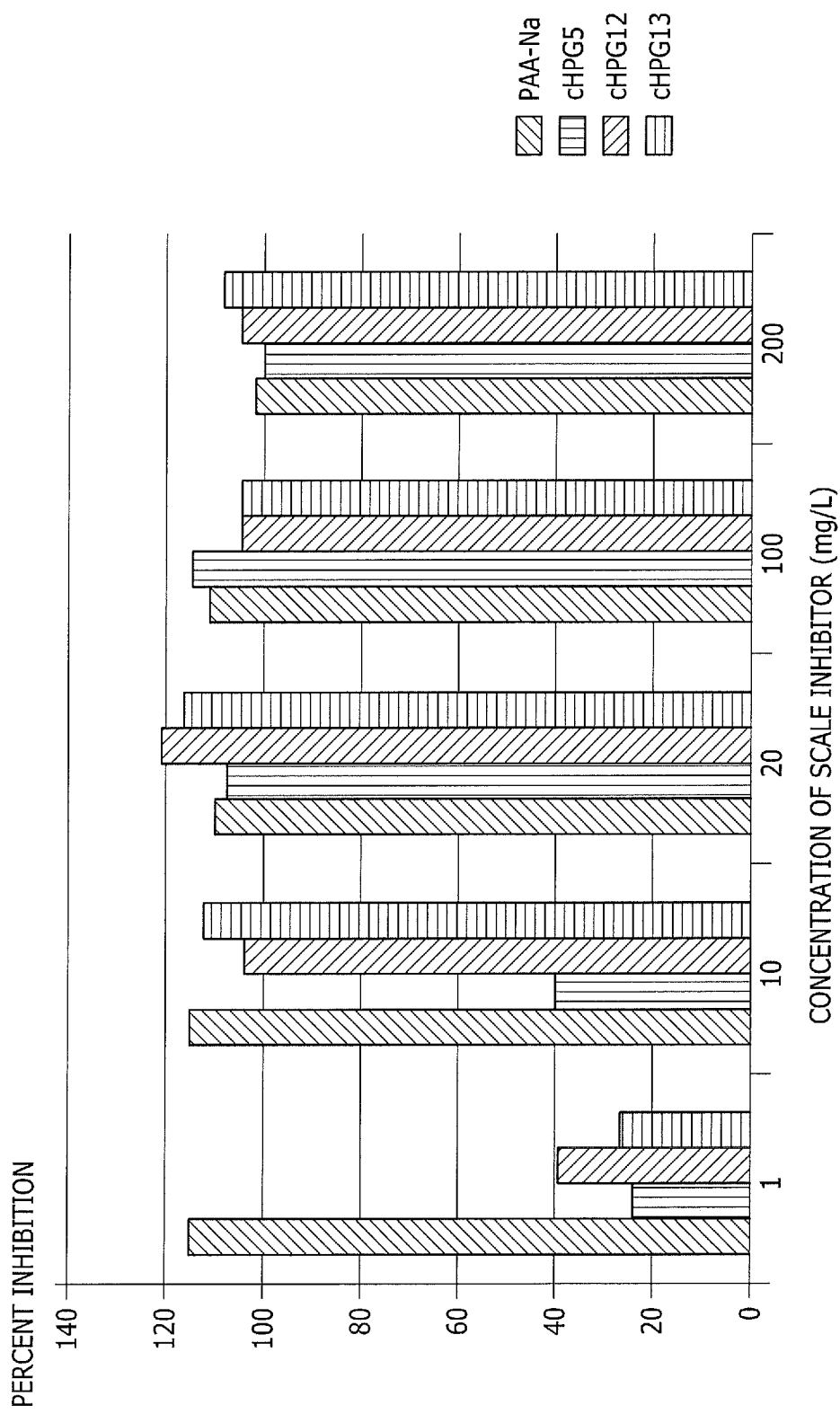
FIG. 2 is a graphical depiction of certain results of the working examples.

The scale inhibition (% inhibition) results for cHPGs and PAA are shown in FIG. 2.
The results in % inhibition are shown in Table 1.

TABLE 1

| Loading of Inhibitor (mg/L) | PAA-Na | cHPG5 | cHPG12 | cHPG13 |
|---|---|---|---|---|
| 1 | 1507 | 1132 | 1194 | 1140 |
| 10 | 1505 | 1196 | 1462 | 1500 |
| 20 | 1491 | 1482 | 1530 | 1516 |
| 100 | 1496 | 1510 | 1469 | 1468 |
| 200 | 1453 | 1378 | 1468 | 1480 |

Initial Ca2+ concentration determined by ICP;
Blank cell #1: 1449.5 ppm
Blank cell #2: 1436.5 ppm
Final Ca2+ concentration determined by ICP:
Blank cell #1: 1009 ppm
Blank cell #2: 1056 ppm Results above show that cHPGs can effectively inhibit $CaSO_4$ scale starting at 10 ppm of the scale inhibitor.

Compatibility Studies in High Divalent Brines

Figure 3:
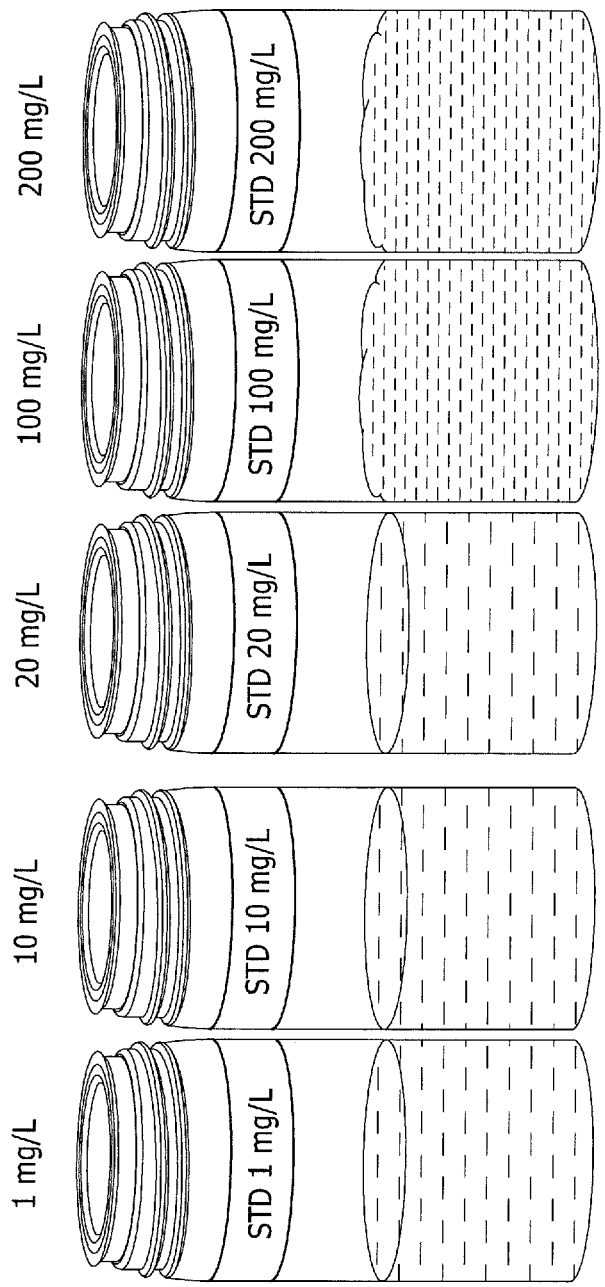
FIG. 3 is an illustration of solution clarity in solutions having from 1 mg/liter to 200 mg/liter of poly acrylic acid sodium salt.
Figure 4:
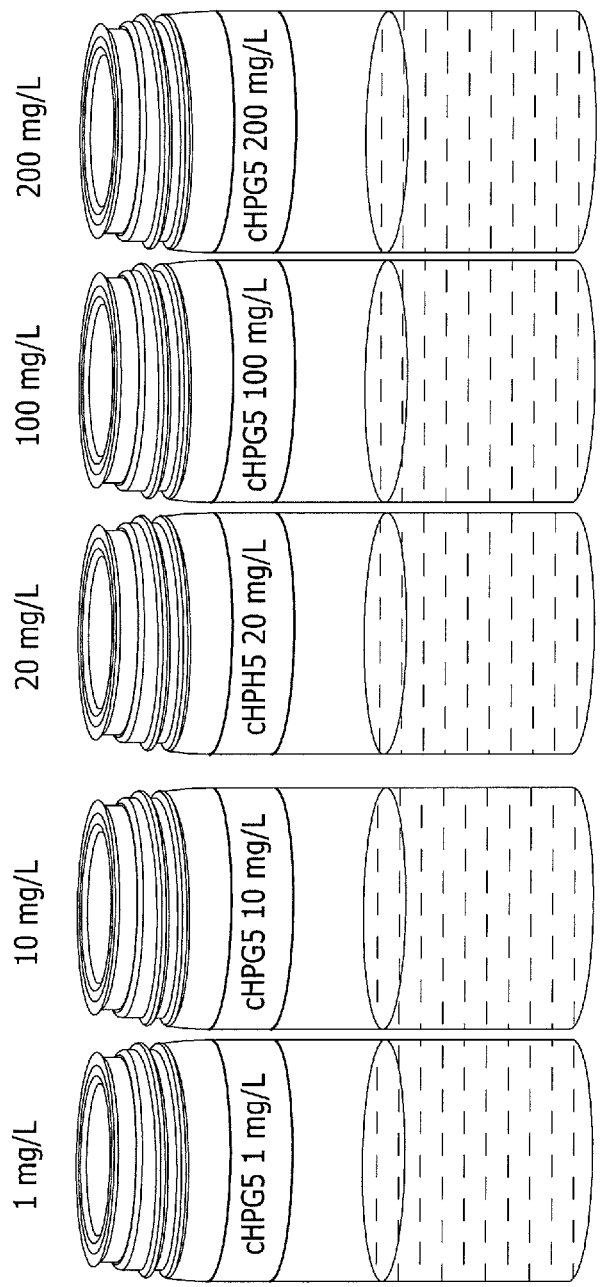
FIG. 4 is an illustration of solution clarity in solutions having from 1 mg/liter to 200 mg/liter of carboxylated hyperbranched polyglycerol.

The compatibility of the cHPGs were also tested against calcium containing brines:
1. Compatibility of PAA vs cHPGs against NACE TM0374 Calcium brine (Ca+2=1440 ppm) are shown in FIGS. 3 and 4.

As can be seen, solutions containing the cHPGS can have higher loadings of the scale inhibitor without any compatibility issues as compared to PAA. PAA shows precipitation at high loadings of the scale inhibitor (100-200 ppm)
2. Compatibility with Shearwater cationic brine ($Ca^{+2}$=36, 900 ppm) The following compatibility studies were done at 10 wt % of the cHPGs
   A=2.2827 g cHPG+20.08 g H2O
   D=1.9859 g cHPG+18.00 g H2O
   E=1.2858 g cHPG+11.60 g H2O
   A, D and E—dissolved in Shearwater cationic brine
   B, C and F—original solutions (dissolved in water)=shown for comparison that no precipitation or incompatibility occurred when the cHPGs were dissolved in the Shearwater cationic brine.
   A—clear, transparent solution—COMPATIBLE
   D—clear, transparent, solution—COMPATIBLE
   E—cHPG not completely soluble—NOT COMPATIBLE Although specific embodiments of the invention have been shown and described, it shall be understood that other embodiments could be substituted therefore without departing from the scope of the invention. Various embodiments have been described. These and other embodiments are within the scope of the following claims.

We claim:
1. A method of scale inhibition treatment of a water system used in oil and gas well applications and industrial water treatment comprising introducing an aqueous scale inhibiting composition into the water system wherein the aqueous scale inhibiting composition comprises a carboxylated hyperbranched polyglycerol polymer having a chemical formula

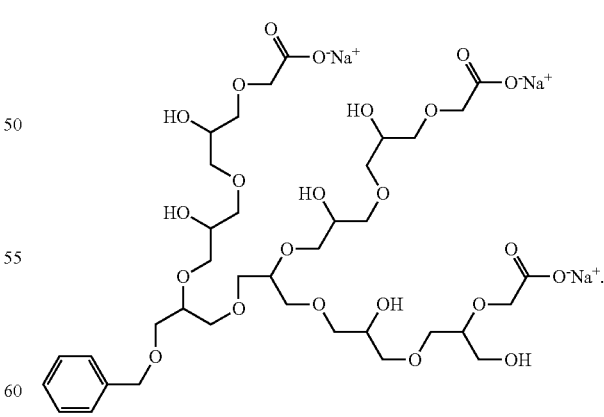

2. The method of claim 1 wherein the polymer concentration ranges 1-60 wt % in said aqueous scale inhibiting compositions.
3. The method of claim 1 wherein said polymer has molecular weight of about 1,000 Da to 50,000 Da.

4. The method of claim 1, wherein the aqueous scale inhibiting composition is used in an aqueous environment having a temperature ranging from about 20° to 300° C.

5. The method of claim 1, wherein the aqueous scale inhibiting composition is used in an aqueous environment having total dissolved solids ranging from about 2000 to 400,000 tds.

6. The method of claim 1, wherein the aqueous scale inhibitors composition is used in an aqueous environment having a pH ranging from about 4 to 8.

* * * * *